(12) United States Patent
Somogyi et al.

(10) Patent No.: US 6,292,680 B1
(45) Date of Patent: Sep. 18, 2001

(54) NON-INVASIVE SENSING OF A PHYSICAL PARAMETER

(76) Inventors: Christopher P. Somogyi, 8925 NE. 13th St., Clyde Hill, WA (US) 98004; Robert N. Golden, 12117 NE. 66th St., Kirkland, WA (US) 98033

( * ) Notice: Subject to any disclaimer, the term of this patent is extended or adjusted under 35 U.S.C. 154(b) by 0 days.

(21) Appl. No.: 09/424,160

(22) PCT Filed: May 20, 1998

(86) PCT No.: PCT/US98/10405
§ 371 Date: Feb. 16, 2000
§ 102(e) Date: Feb. 16, 2000

(87) PCT Pub. No.: WO98/52466
PCT Pub. Date: Nov. 26, 1998

Related U.S. Application Data
(60) Provisional application No. 60/047,307, filed on May 21, 1997.

(51) Int. Cl.[7] .................................................... A61B 5/05
(52) U.S. Cl. ...................... 600/407; 600/409; 600/481; 600/529; 600/549; 600/587
(58) Field of Search .................................. 600/9–15, 481, 600/485–486, 504, 505, 508–509, 513, 529, 538, 561, 407, 409, 549, 587

(56) References Cited

U.S. PATENT DOCUMENTS

| | | | |
|---|---|---|---|
| 5,176,618 | * 1/1993 | Freedman | 600/12 |
| 5,425,382 | 6/1995 | Golden et al. | 128/899 |
| 5,622,169 | 4/1997 | Golden et al. | 128/653.1 |
| 5,879,297 | 3/1999 | Haynor et al. | 600/407 |

* cited by examiner

Primary Examiner—John P. Lacyk
Assistant Examiner—Ryan Carter
(74) Attorney, Agent, or Firm—Michael J. Donohue; Seed IP Law Group PLLC

(57) ABSTRACT

There is disclosed a method and device for non-invasively sensing a physical parameter within the body of a patient by employing a magnetically-based sensing device and monitoring device. The magnetically-based sensing device has a first magnet and a second magnet which generate a combined magnet field. The first and second magnets are positioned such that a change in a physical parameter causes a change in the combined magnet field, which change is monitored by the monitoring device.

16 Claims, 4 Drawing Sheets

NON-INVASIVE SENSING OF A PHYSICAL PARAMETER

This application claims the benefit of provisional application 60/047,307 filed May 21, 1997.

TECHNICAL FIELD

This invention is generally directed to a device and method for non-invasively sensing a physical parameter and, more specifically to the monitoring of a magnetically-based sensing device to sense a change in a physical parameter.

BACKGROUND OF THE INVENTION

There are numerous medical devices which are implanted into the body of animals, including humans (hereinafter collectively referred to as "patients"). These devices are resident for periods of time ranging from several days to the lifetime of the patient. Such implanted devices encompass a wide range of applications, including (but not limited to) artificial joints, artificial ligaments, artificial tendons, bone implants, orthotic devices, orthopedic correctional and supporting devices (e.g., screws and braces), shunts, stents, pumps, collection reservoirs, drug delivery depots, temperature sensors, pressure sensors, temporary surgical staples, and the like.

Such implanted devices may be related to one or more changing physical parameters. These changes may be associated with, for example, a feature of the device, a result of a physiological impact on the implanted device, or may be indicative of the success or failure of the implanted device. In this context, representative changing physical parameters include temperature, strain, oscillation, pressure, volume, flow, acceleration, angular momentum, angular velocity, chemical composition, pH, ionic content, changing material characteristics of an anatomical structure or of the implantable, and the like.

There is clinical value in being able to measure certain physical parameters associated with physiological processes and anatomical conditions. This measurement process involves four parts: (1) the sensing of a condition or a changing condition; (2) the transduction of the sensor input to an appropriate energy or signal format; (3) signal conditioning to make the transduced signal suitable for transmission; and (4) the reporting or transmission of the information. There exist systems to address all four parts, though these are usually made of discrete components dedicated to each of the four parts. For example, an implanted thermistor would measure temperature, convert the temperature change into an impedance change, registering a voltage drop, the numerical value of which is transmitted in coded format via dynamic electromagnetic signal. Similarly, an implanted blood pressure monitoring device may consist of an air-filled dome over a silicon-based pressure sensor which converts strain to a change of an electrical parameter. This change is measured, coded, transmitted via high frequency electromagnetic emission. For both examples, a receiver external to the body would register the emitted coded signal, providing decoding, interpretation, and data display.

Certain physiological and anatomical parameters can also be detected by entirely non-invasive means, such as magnetic resonance imaging (MRI), ultrasound, and X-ray techniques. However, these methods have come to rely more and more on the infusion of certain contrast agents in the subject area. Such infusion is an invasive process.

While such sensing and transmission techniques have shown to be effective, there is still a need in the art for improved devices and methods for non-invasively sensing changing physical parameters. The present invention fulfills these needs, and provides further related advantages.

SUMMARY OF THE INVENTION

In brief, this invention discloses a method and device for non-invasive sensing of a physical parameter (or parameters) within the body of a patient by employing a magnetically-based sensing device and a monitoring device. As used herein, the term "non-invasive" means that sensing of the physical parameter is performed without requiring access to or removal of the sensing device, and without physical contact between the sensing device and the monitoring device. (It should be noted, however, that location of the sensing device within the body of the patient typically constitutes an invasive procedure.) Also as used herein, the term "physical parameter" includes (but is not limited to) temperature, strain, oscillation, pressure, volume, flow, acceleration, angular momentum, angular velocity, chemical composition, pH, ionic content, and/or changing material characteristics of an anatomical structure or of an implanted device.

The magnetically-based sensing device of this invention comprises a first magnet and a second magnet in close proximity thereto. The first magnet generates a first magnetic field, the second magnet generates a second magnetic field, and the sum of the first and second magnetic fields generate a combined magnetic field. The first magnet is associated with the implanted device itself, or with tissue (including bone) associated therewith while the second magnet is positioned such that a change in a physical parameter results in displacement of the first and/or second magnet, thus changing the combined magnetic field. Such magnetically-based sensing devices may take a variety of forms, as disclosed in greater detail in the following detailed description.

The monitoring device is any suitable apparatus capable of detecting the combined magnetic field of the magnetically-based sensing device. As mentioned above, changes in the combined magnetic field strength indicate a changed or changing physical parameter. As with the sensing device, the monitoring device may also take a variety of forms as disclosed in greater detail in the following detailed description.

In another embodiment of this invention, a method is disclosed for sensing a physical parameter by associating a first magnet with, for example, an implanted device, and positioning a second magnet in close proximity to the first magnet such that the sum of the first and second magnetic fields yields a combined magnetic field. This combined magnetic field is then monitored, typically over a period of time, to detect changes in the physical parameter of interest.

These and other aspects of the present invention will be better understood upon reference to the following detailed description and accompanying drawings.

DETAILED DESCRIPTION OF THE INVENTION

As indicated above, the present invention is directed to a magnetically-based sensing device and a monitoring device for non-invasively sensing a physical parameter, and to methods related thereto. The sensing device comprises a first magnetic material and a second magnetic material in close proximity thereto. As used herein, the term "magnetic material" means any material which generates a magnetic field gradient capable of detection by the monitoring device. Such magnetic material may be in the form of a rigid or non-rigid (e.g., malleable) material. For purpose of convenience, the term "magnet" is used herein synonymously with the phrase "magnetic material."

In one embodiment of this invention, the first and second magnets are in opposition or "inverse alignment." In other words, the magnetic field gradients of the first and second magnets are oriented such that they partially or completely cancel out. For example, the first and second magnets may be aligned such that the north pole of the first magnet is proximal to the south pole of the second magnet (and visa versa—that is, the south pole of the first magnet is proximal to the north pole of the second magnet). In this manner, the magnetic field gradients of both magnets effectively cancel each other out, resulting in a reduced (e.g., zero or near-zero) magnetic field.

By holding the first magnet stationary or steady, and moving the second magnet out of inverse alignment, an increasing magnetic field is measurable. Conversely, if the first and second magnets were initially aligned out of inverse alignment, and then moved into inverse alignment, a decreasing magnetic field is measurable. Such movement may occur linearly or rotationally along any axis of the magnet. In the context of an implanted device, the first magnet may be associated with a bone, while the second magnet is positioned on an orthotic device such that the two magnets are in complete or partial inverse alignment as illustrated in FIG. 1.

Figure 1A:
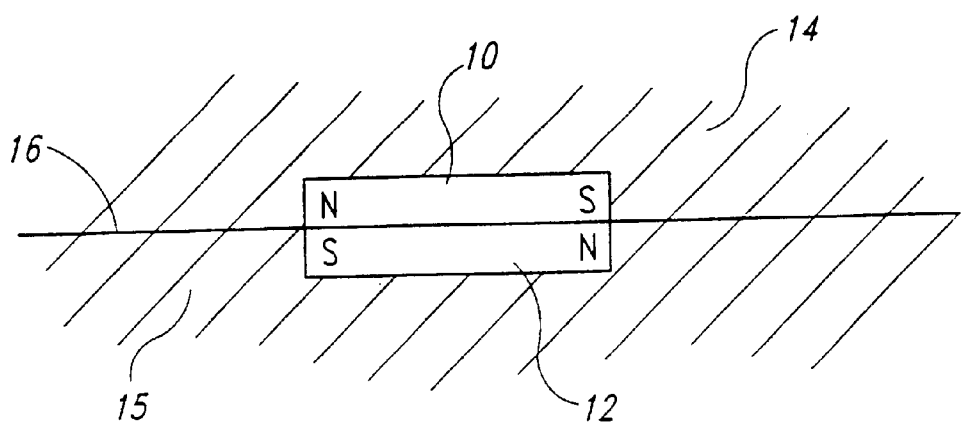
FIGS. 1A and 1B illustrate a representative embodiment of this invention wherein two magnets are in inverse alignment such that movement of one magnet relative to the other results in an increased combined magnetic field.
Figure 1B:
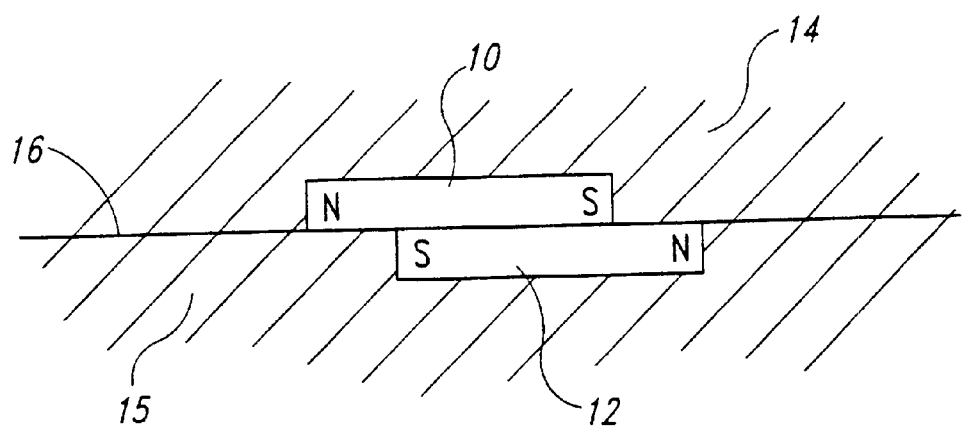

Referring to FIG. 1A, first magnet 10 is inversely aligned with second magnet 12 such that the magnetic field gradients of each magnet completely or partially cancel out—that is, the north pole ("N") of magnet 10 is proximal to the south pole ("S") of magnet 12 and, conversely, the south pole of magnet 10 is proximal to the north pole of magnet 12. Magnet 10 is associated with substrate 14 which, in one embodiment, may be bone, and magnet 12 is associated with substrate 15 which, in one embodiment, may be an orthotic device. Displacement of substrate 14 relative to substrate 15 along an axis parallel to contact surface 16 is illustrated in FIG. 1B. By such displacement, the combined magnetic field of magnet 10 and magnet 12 will have increased since the two magnets are no longer in the same degree of inverse alignment. Thus, by monitoring the combined magnetic field, displacement of substrate 14 relative to substrate 15 may be detected.

It should be understood that a change in a physical parameter, such as displacement of substrate 14 relative to substrate 15, may result in either an increase or decrease in the combined magnetic field. For example, while displacement from the orientation of FIG. 1A to FIG. 1B results in an increase in the combined magnetic field, displacement from the orientation of FIG. 1B to that of FIG. 1A causes a decrease in the same. Thus, any change in the combined magnetic field evidences a change in the physical parameter at issue, and is within the scope of this invention.

In another embodiment, a first magnet is associated with the implanted device itself, such as a catheter, and a second magnet is positioned in inverse alignment thereto such that a change in a physical parameter alters the combined magnetic field of the two magnets. For example, referring to FIG. 2A, first magnet 20 is affixed to catheter wall 24, and second magnet 22 is affixed to bladder 28 which, in turn, is affixed to catheter wall 25. At an initial pressure ($P_1$) the first and second magnets are oriented as disclosed in FIG. 2A. However, upon exposure to a lower pressure ($P_0$), bladder 28 expands as illustrated in FIG. 2B, causing magnet 22 to assume a more inversely oriented relationship to magnet 20, thus decreasing the combined magnetic field. Conversely, at a higher pressure ($P_2$), bladder 28 decreases in volume as illustrated in FIG. 2C, resulting in an increase in the combined magnetic field due to movement of magnet 22 away from magnet 20. Such changes in the combined magnetic field may be calibrated to indicate relative or absolute pressure levels, or rate of change of the same. Similarly, position of the medical device or tube within the patient can be detected, such as movement from the vena cava to the atrium.

Figure 2A:
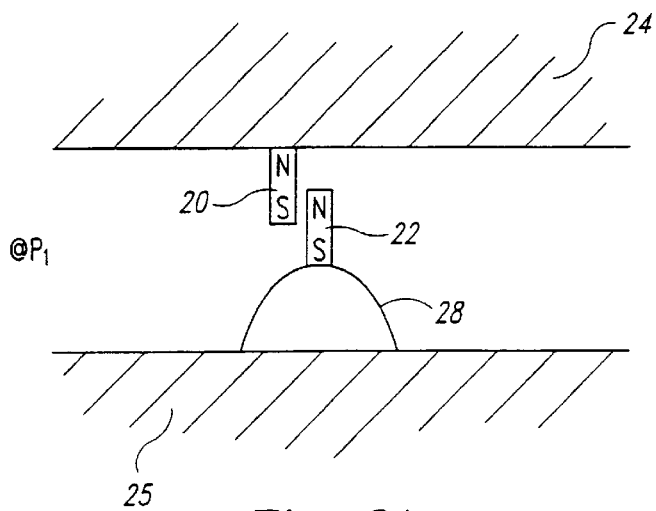
FIGS. 2A, 2B and 2C illustrate a representative embodiment of this invention wherein a change in a physical parameter alters the combined magnetic field of two magnets.
Figure 2B:
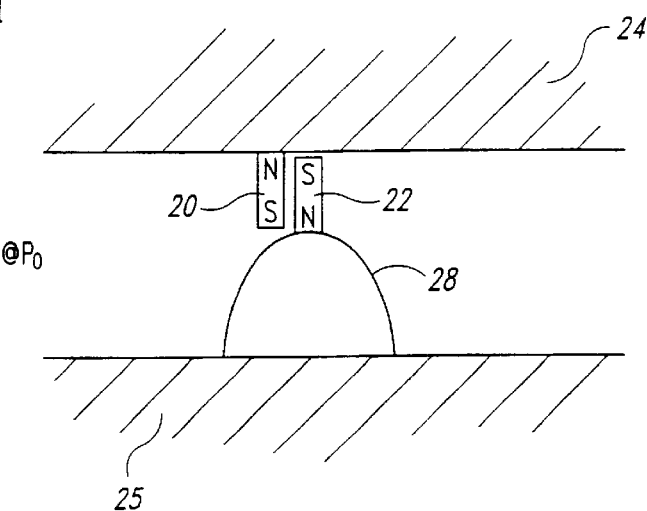
Figure 2C:
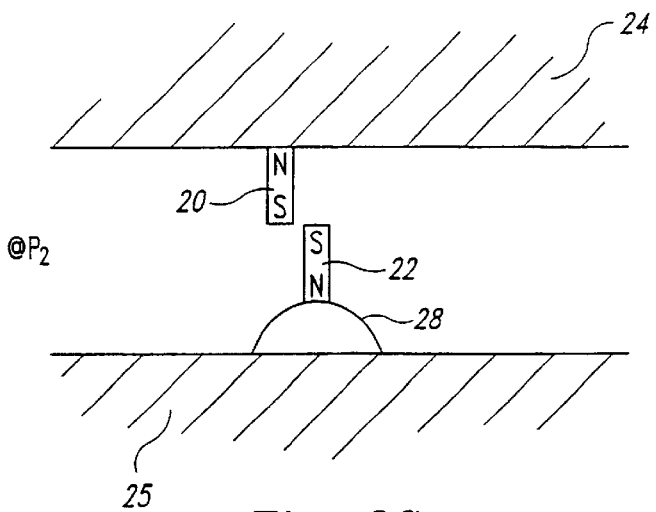

The embodiment illustrated in FIG. 2A may also be used to measure flow rates of a substance within the volume between walls 24 and 25. Thus, as a material flows past these magnets, the resulting chance in the combined magnetic field due to displacement of magnet 22 relative to magnet 20 is proportional to the flow rate of the material.

Figure 3A:
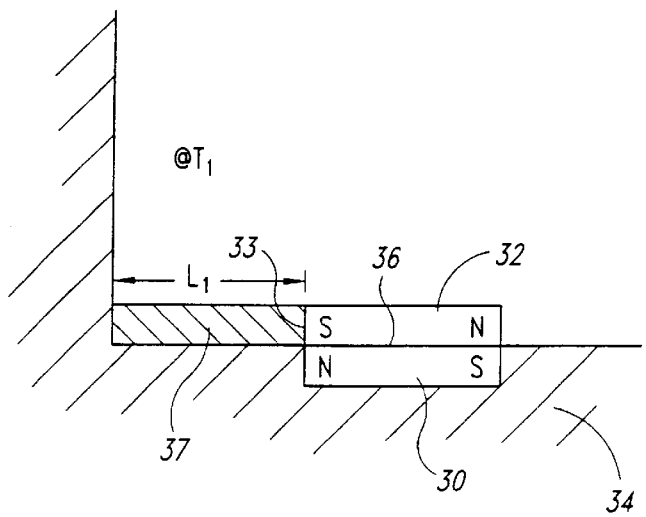
FIGS. 3A, 3B and 3C illustrate a representative embodiment of this invention wherein a first magnet is associated with a substrate in a fixed orientation, while a second magnet is displaceable relative thereto.
Figure 3B:
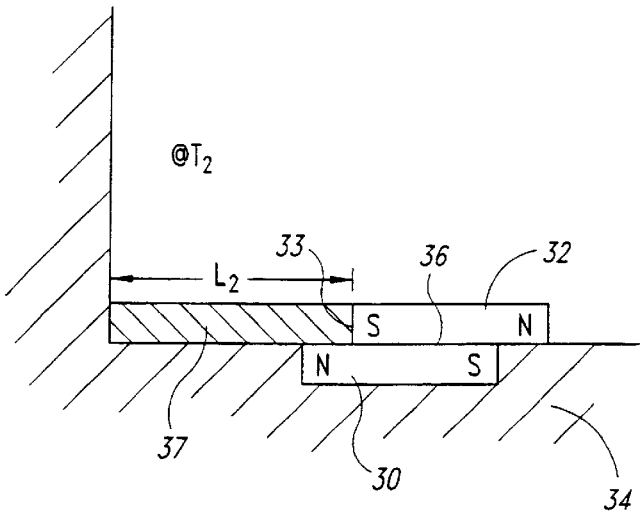
Figure 3C:
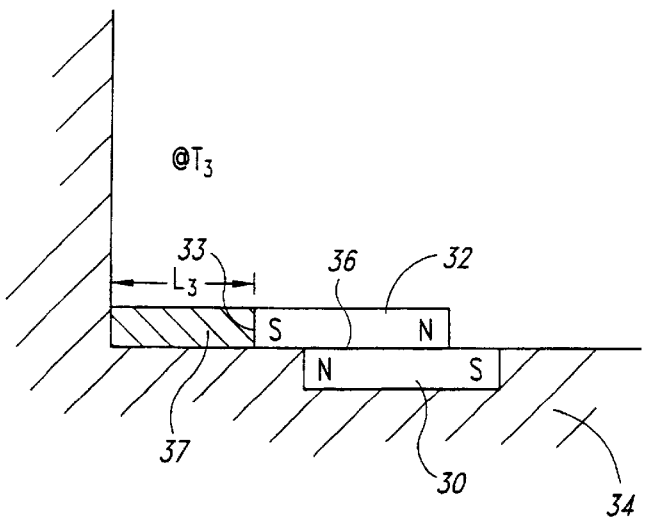

In still another embodiment, first magnet 30 is associated with substrate 34 in a fixed orientation as illustrated in FIG. 3A. Second magnet 32 is inversely oriented to the first magnet, and displaceable along an axis parallel to surface contact line 36. End 33 of magnet 32 is in contact with a temperature-sensitive material 37 having a length ($L_1$) at a first temperature ($T_1$). Such temperature-sensitive materials, including precise dimensional changes of the same, are well known. Upon a change in temperature from $T_1$ to a second temperature ($T_2$), the temperature-sensitive material 37 increases to a second length ($L_2$), resulting in displacement of magnet 32 as illustrated by FIG. 3B. Similarly, upon a change in temperature from $T_1$ to third temperature ($T_3$), the length of temperature-sensitive material 37 decreases to a third length ($L_3$), resulting in displacement of magnet 32 as illustrated in FIG. 3C. Such displacement of magnet 32 relative to magnet 30 results in a change of the combined magnetic field, providing a means to measure temperature.

Figure 4A:
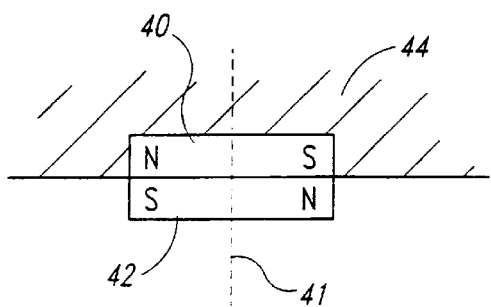
FIGS. 4A, 4B, 4C and 4D illustrate a representative embodiment of this invention wherein a first magnet is fixed to a substrate, and a second magnet is rotatably affixed thereto.
Figure 4B:
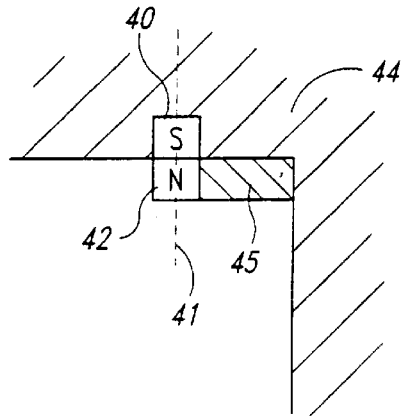
Figure 4C:
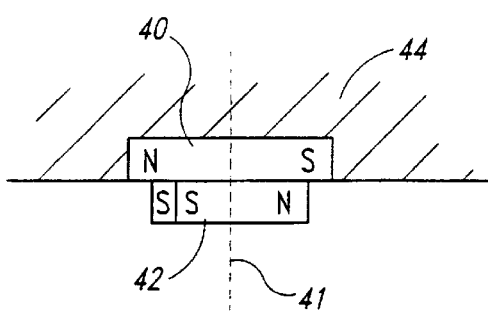
Figure 4D:
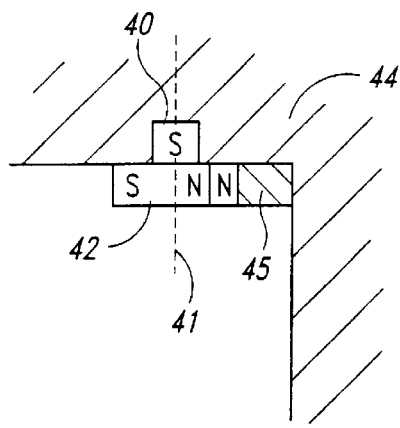

In a further embodiment, first magnet 40 is fixed to substrate 44 as illustrated in FIG. 4A. Second magnet 42 is rotatably attached about axis 41 to first magnet 40. Depletable material 45 is affixed to the north pole region of magnet 42 as illustrated by FIG. 4B, which is a side-view of FIG. 4A. As depletable material 45 is depleted, magnet 42 rotates about axis 41 as illustrated in FIGS. 4C and 4D (FIG. 4D being a side-view of the FIG. 4C). Such rotation results in a change in the combined magnetic field which, in turn, provides information concerning the remaining amount of depletable material.

In the above embodiments, the orientation of the first and second magnets have generally been in some degree of inverse alignment. In the practice of this invention, orientation in this manner is preferred since two magnets are more readily placed in close physical proximity when the north pole of the first magnet is proximal to the south pole of the second magnet (and visa versa). However, this invention is not limited in this manner. Rather, in other embodiments of this invention, the first and second magnet may be oriented such that the north pole of the first magnet is proximal to the north pole of the second magnet.

In one embodiment of proximal polar alignment, one magnet is firmly attached to a substrate such as a catheter structural element. The second magnet is aligned such that its north pole is adjacent to the north pole of the first magnet. The natural repulsive forces are resisted by a mechanical force keeping the magnets in this alignment. Such force may be provided by a spring, elastic member, or frame. On encountering a change in physical parameter such as the force of a blood pressure pulse, the structural element forcing the second magnet into proximal alignment with the first magnet is caused to undergo a displacement. This displacement allows the natural repulsive force to cause a displacement of the second magnet relative to the first. The movement of the second magnet then changes the summed magnetic field such that a detector can measure or note the change. By proper calibration, the field change can be related to a measurement of blood pressure force.

In addition, it should be understood that more than two magnets may be employed in the practice of this invention. For example, if a first, second and third (or more) magnets are used, the combined magnetic field reflects contributions from all three (or more) magnets. In this embodiment, changes in the combined magnetic field reflects displacement between any two (or more) magnets.

As mentioned above, a change in the combined magnetic field are used to monitor a physical parameter. In the context of this invention, any monitoring device capable of measuring the combined field may be employed in the practice of this invention. In a preferred embodiment, the monitoring device is the magnetic field detector disclosed in U.S. Pat. Nos. 5,425,382 and 5,622,169 to Golden and Silverstein (hereby incorporated by reference in their entirety). The Golden and Silverstein detector employs two static magnetic field strength sensors configured geometrically to null detection of ambient, homogeneous magnetic fields (such as the earth's magnetic field), yet are capable of detecting the combined magnetic field of the first and second (or more) magnets.

More specifically, the Golden and Silverstein detector is an active, electronic instrument, and can detect the relatively small combined magnetic field produced by the first and second magnets at distances ranging from several centimeters to several decimeters. It also is capable of detecting and displaying the orientation of the combined field gradient (i.e., the dipole). In this manner, the strength of the combined field, the orientation, and any movement or oscillation of the same can be monitored. In certain embodiments, such as those disclosed in FIGS. 3 and 4, a change in the orientation of the combined magnetic field also results upon displacement of the second magnet relative to the first magnet. Accordingly, in the context of this invention the monitoring device can sense the changing physical parameter at issue by measuring a change in strength and/or orientation of the combined magnetic field.

Suitable magnets of this invention are electromagnets, as well as permanent magnets that require no power source. In the context of permanent magnets, the undesirable electrical connections necessary for the use of a power source are avoided. Thus, there is no risk of shock to (or possible electrocution of) a patient due to the magnet. Suitable permanent magnets are generally relatively small, rare-earth magnets, and include rare-earth magnets such as samarium cobalt and neodymium iron boron, both of which generate high field strengths per unit volume. While magnets which generate a high field strength for their size are preferred, weaker magnets such as Alnico or ceramic may also be utilized.

Furthermore, suitable magnets of this invention also include rigid or non-rigid magnets. Non-rigid magnets include (but are not limited to) suspensions of magnetic particles, malleable forms of magnetic material (such as a putty), and magnets bound in a biodegradable material (e.g., dissolvable magnets). Rigid magnets are available from a variety of sources, including Dexter Corp. (Fremont, Calif.). Non-rigid magnets are generally comprised of a plurality of magnet particles contained within a suspension or slurry, or within a more solid, but malleable, substance. Suitable suspension or slurries include (but are not limited to) magnetic particles within a fluid such as oil, water, glycerin, alcohol, fluid polymers and the like. More solid, yet malleable, magnets include magnetic particles within a putty, polymer, silicone, highly viscous liquid and the like. Suitable polymers include those that are solid at room temperature, but malleable at body temperature. When non-rigid magnets in the form of suspension or slurries are employed, they are typically confined within an appropriate enclosure. More viscous non-rigid magnets, such as putties and the like, are less susceptible to leakage, but may still benefit from an appropriate enclosure.

From the foregoing, it will be appreciated that, although specific embodiments of this invention have been described herein for purposes of illustration, various modifications may be made without deviating from the spirit and scope of the invention. Accordingly, the invention is not limited except by the appended claims.

We claim:

1. A method for sensing a physical parameter within the body of a patient, comprising:

associating a first magnet with a tissue substrate within the body of the patient, wherein the first magnet generates a first magnetic field;

positioning a second magnet at an initial orientation with, and in close proximity to, the first magnet such that a change in the physical parameter alters the initial orientation between the first magnet and second magnet, wherein the second magnet generates a second magnetic field and the initial orientation is such that the first and second magnets are selectively oriented in alignment such that the first and second magnetic fields combine additively or in inverse alignment such that the first and second magnetic fields are substantially canceled by each other, the sum of the first and second magnetic fields yields an initial combined magnetic field;

measuring the initial combined magnetic field; and monitoring the combined magnetic field over a period of time to sense a change in the physical parameter.

2. The method of claim 1 wherein the tissue substrate is bone and the second magnet is associated with an orthotic device.

3. The method of claim 2 wherein the physical parameter is movement between the bone and orthotic device.

4. The method of claim 1 wherein a change in the physical parameter alters the initial orientation between the first magnet and second magnet such that the initial combined magnetic field is increased in strength over time.

5. The method of claim 1 wherein a change in the physical parameter alters the initial orientation between the first magnet and second magnet such that the initial combined magnetic field is decreased in strength over time.

6. The method of claim 1 wherein a change in the physical parameter alters the initial orientation between the first magnet and second magnet such that the initial combined magnetic field is changed with regard to orientation of the same over time.

7. A method for sensing a physical parameter within the body of a patient, comprising:

associating a first magnet with a device implanted within the body of the patient, wherein the first magnet generates a first magnetic field;

positioning a second magnet at an initial orientation with, and in close proximity to, the first magnet such that a change in the physical parameter alters the initial orientation between the first magnet and second magnet, wherein the second magnet generates a second magnetic field and the initial orientation is such that the first and second magnets are selectively oriented in alignment such that the first and second magnetic fields combine additively or in inverse alignment such that the first and second magnetic fields are substantially canceled by each other, the sum of the first and second magnetic fields yields an initial combined magnetic field;

measuring the initial combined magnetic field; and monitoring the combined magnetic field over a period of time to sense a change in the physical parameter.

8. The method of claim 7 wherein the device implanted into the body of the patient is selected from catheters, tubes, surgical staples, tissue joining devices, shunts, stents, artificial valves, artificial vessels, esophagus, trachea, tags and markers.

9. The method of claim 7 wherein the physical parameter is selected from strain, pressure, force, impact, volume, temperature, rotation, displacement, flow rate, oscillation frequency and damping coefficient.

10. The method of claim 7 wherein a change in the physical parameter alters the initial orientation between the first magnet and second magnet such that the initial combined magnetic field is increased in strength over time.

11. The method of claim 7 wherein a change in the physical parameter alters the initial orientation between the first magnet and second magnet such that the initial combined magnetic field is decreased in strength over time.

12. Thee method of claim 7 wherein a change in the physical parameter alters the initial orientation between the first magnet and second magnet such that the initial combined magnetic field is chanted with regard to orientation of the same over time.

13. A magnetically-based sensor system for sensing a physical parameter within the body of a patient, the system comprising a sensing device having a first magnet which generates a first magnetic field and a second magnet which generates a second magnetic field in initial orientation with, and in close proximity to, the first magnet, with the first and second magnets being initially oriented in alignment with each other or in inverse alignment with each other such that a change in the physical parameter alters the initial orientation between the first magnet and second magnet, wherein the sum of the first and second magnetic fields yields an initial combined magnetic field detectable by a magnetic detector, and a monitoring device capable of measuring the combined magnetic field.

14. The system of claim 13 wherein the magnetically-based sensing device is implantable.

15. The system of claim 14 wherein the device is selected from catheters, tubes, surgical staples, tissue joining devices, shunts, stents, artificial valves, artificial vessels, esophagus, trachea, tags and markers.

16. The system of claim 13 wherein the physical parameter is selected from strain, pressure, force, impact, volume, temperature, rotation, displacement, flow rate, oscillation frequency and damping coefficient.

* * * * *

UNITED STATES PATENT AND TRADEMARK OFFICE
CERTIFICATE OF CORRECTION

| | | |
|---|---|---|
| PATENT NO. | : 6,292,680 B1 | Page 1 of 1 |
| APPLICATION NO. | : 09/424160 | |
| DATED | : September 18, 2001 | |
| INVENTOR(S) | : Christopher P. Somogyi et al. | |

It is certified that error appears in the above-identified patent and that said Letters Patent is hereby corrected as shown below:

Column 1, Line 7:

Please insert,

--STATEMENT OF GOVERNMENT INTEREST
This invention was made with government support under SBIR Grant No. RR10676-03 awarded by the National Center of Research resources of the National Institutes of Health. The government has certain rights in this invention.--.

Signed and Sealed this
Fifth Day of March, 2013

Teresa Stanek Rea
*Acting Director of the United States Patent and Trademark Office*